(12) United States Patent
Eversull et al.

(10) Patent No.: US 7,575,569 B2
(45) Date of Patent: Aug. 18, 2009

(54) APPARATUS AND METHODS FOR DELIVERING STEM CELLS AND OTHER AGENTS INTO CARDIAC TISSUE

(75) Inventors: Christian S. Eversull, Palo Alto, CA (US); Stephen A. Leeflang, Sunnyvale, CA (US); Christine P. Ventura, San Jose, CA (US); Nicholas J. Mourlas, Mountain View, CA (US)

(73) Assignee: Medtronic, Inc., Minneapolis, MN (US)

( * ) Notice: Subject to any disclaimer, the term of this patent is extended or adjusted under 35 U.S.C. 154(b) by 236 days.

(21) Appl. No.: 11/465,109

(22) Filed: Aug. 16, 2006

(65) Prior Publication Data

US 2007/0083187 A1 Apr. 12, 2007

Related U.S. Application Data

(60) Provisional application No. 60/708,746, filed on Aug. 16, 2005.

(51) Int. Cl.
*A61M 31/00* (2006.01)
(52) U.S. Cl. .................... 604/103.01; 604/509
(58) Field of Classification Search ......... 604/508–509, 604/52, 96.01, 102.01–102.03, 103.01, 103.06
See application file for complete search history.

(56) References Cited

U.S. PATENT DOCUMENTS

| | | | |
|---|---|---|---|
| 4,392,853 A | 7/1983 | Muto | |
| 4,401,433 A | 8/1983 | Luther | |
| 4,406,656 A | 9/1983 | Hattler et al. | |
| 4,451,256 A | 5/1984 | Weikl et al. | |
| 4,569,347 A | 2/1986 | Frisbie | |
| 4,581,017 A | 4/1986 | Sahota | |
| 4,601,713 A | 7/1986 | Fuqua | |
| 4,710,181 A | 12/1987 | Fuqua | |
| 4,738,666 A | 4/1988 | Fuqua | |
| 4,921,479 A | 5/1990 | Grayzel | |

(Continued)

FOREIGN PATENT DOCUMENTS

EP 818214 4/2007

(Continued)

OTHER PUBLICATIONS

USPTO Office Action for co-pending U.S. Appl. No. 10/958,034 dated Oct. 19, 2006.

(Continued)

*Primary Examiner*—Kevin C Sirmons
*Assistant Examiner*—Andrew M Gilbert (57) ABSTRACT

Apparatus, systems, and methods are provided for delivering stem cells or other agents to cardiac tissue surrounding a cardiac vessel or to tissue adjacent other body lumens. The apparatus includes an expandable member and a source of one or more agents communicating with a lumen extending between proximal and distal ends of the apparatus. The distal end of the apparatus is advanced through one or more body lumens until the distal end is disposed within or adjacent the target body lumen. The target body lumen is sealed, e.g., by expanding the expandable member, thereby isolating the target body lumen. One or more agents are delivered into the target body lumen with sufficient pressure to extravasate the one or more agents into tissue surrounding the target body lumen.

22 Claims, 7 Drawing Sheets

U.S. PATENT DOCUMENTS

| | | | |
|---|---|---|---|
| 5,015,239 A | 5/1991 | Browne | |
| 5,201,756 A | 4/1993 | Horzewski et al. | |
| 5,234,425 A | 8/1993 | Fogarty et al. | |
| 5,254,084 A | 10/1993 | Geary et al. | |
| 5,256,150 A | 10/1993 | Quiachon et al. | |
| 5,275,151 A | 1/1994 | Shockey et al. | |
| 5,304,134 A | 4/1994 | Kraus et al. | |
| 5,395,349 A | 3/1995 | Quiachon et al. | |
| 5,413,560 A | 5/1995 | Solar | |
| 5,431,676 A | 7/1995 | Dubrul et al. | |
| 5,472,418 A | 12/1995 | Palestrant | |
| 5,573,517 A | 11/1996 | Bonutti et al. | |
| 5,618,267 A | 4/1997 | Palestrant | |
| 5,674,240 A | 10/1997 | Bonutti et al. | |
| 5,713,853 A * | 2/1998 | Clark et al. | 604/509 |
| 5,735,831 A * | 4/1998 | Johnson et al. | 604/523 |
| 5,749,889 A | 5/1998 | Bacich et al. | |
| 5,772,628 A | 6/1998 | Bacich et al. | |
| 5,810,776 A | 9/1998 | Bacich et al. | |
| 5,827,227 A | 10/1998 | DeLago | |
| 5,904,670 A * | 5/1999 | Schreiner | 604/523 |
| 5,911,702 A | 6/1999 | Romley | |
| 5,944,691 A | 8/1999 | Querns, et al. | |
| 5,961,499 A | 10/1999 | Bonutti et al. | |
| 5,997,508 A | 12/1999 | Lunn et al. | |
| 6,007,517 A | 12/1999 | Anderson | |
| 6,048,332 A * | 4/2000 | Duffy et al. | 604/103.08 |
| 6,090,072 A | 7/2000 | Kratoska et al. | |
| 6,120,477 A | 9/2000 | Campbell et al. | |
| 6,183,443 B1 | 2/2001 | Kratoska et al. | |
| 6,197,016 B1 | 3/2001 | Fourkas et al. | |
| 6,312,406 B1 | 11/2001 | Jayaraman | |
| 6,338,730 B1 | 1/2002 | Bonutti et al. | |
| 6,361,528 B1 * | 3/2002 | Wilson et al. | 604/500 |
| 6,602,241 B2 | 8/2003 | Makower et al. | |
| 6,652,492 B1 | 11/2003 | Bell et al. | |
| 6,814,715 B2 | 11/2004 | Bonutti et al. | |
| 2001/0007927 A1 | 7/2001 | Koblish et al. | |
| 2001/0039418 A1 | 11/2001 | Schaer | |
| 2001/0041909 A1 | 11/2001 | Tsugita et al. | |
| 2001/0053919 A1 | 12/2001 | Kieturakis et al. | |
| 2002/0095117 A1 | 7/2002 | Wilson et al. | |
| 2002/0099431 A1 | 7/2002 | Armstrong et al. | |
| 2002/0165598 A1 | 11/2002 | Wahr et al. | |
| 2003/0004540 A1 | 1/2003 | Linder et al. | |
| 2003/0065353 A1 | 4/2003 | Horzewski et al. | |
| 2003/0233115 A1 * | 12/2003 | Eversull et al. | 606/194 |
| 2004/0005295 A1 | 1/2004 | Lee et al. | |
| 2004/0006344 A1 | 1/2004 | Nguyen et al. | |
| 2004/0073286 A1 | 4/2004 | Armstrong et al. | |
| 2004/0087968 A1 | 5/2004 | Core | |
| 2005/0085842 A1 * | 4/2005 | Eversull et al. | 606/191 |
| 2005/0149105 A1 | 7/2005 | Leeflang et al. | |

FOREIGN PATENT DOCUMENTS

| | | |
|---|---|---|
| WO | 84/01512 | 4/1984 |
| WO | 97/29680 | 8/1997 |
| WO | 98/29026 | 7/1998 |
| WO | 0103766 | 1/2001 |
| WO | 03090834 | 11/2003 |

OTHER PUBLICATIONS

USPTO Office Action for co-pending U.S. Appl. No. 10/958,034 dated Dec. 13, 2006.

PCT/US07/75640 International Search Report and Written Opinion, dated of mailing Jul. 14, 2008.

* cited by examiner

APPARATUS AND METHODS FOR DELIVERING STEM CELLS AND OTHER AGENTS INTO CARDIAC TISSUE

This application claims benefit of provisional application Ser. No. 60/708,746 filed Aug. 16, 2005, the entire disclosure of which is expressly incorporated by reference herein.

FIELD OF THE INVENTION

The present invention relates generally to apparatus and methods for delivering agents and/or instruments during a medical procedure, and more particularly, to apparatus and methods for delivering agents, e.g., therapeutic agents, such as stem cells, or diagnostic agents, into tissue within a patient, e.g., within cardiac tissue surrounding one or more vessels.

BACKGROUND

Minimally invasive procedures have been implemented in a variety of medical settings, e.g., for vascular interventions, such as angioplasty, stenting, embolic protection, electrical heart stimulation, heart mapping and visualization, and the like. These procedures generally rely on accurately navigating and placing instruments within a patient's vasculature.

During such procedures, a target vessel may be accessed using a guidewire advanced through the intervening vasculature into the target vessel, thereby providing a "railway" to the vessel. One or more instruments, e.g., catheters, sheaths, and the like, may be advanced over the guidewire or "rail" into the vessel. Thus, a diagnostic and/or therapeutic procedure may be performed by advancing one or more instruments over this railway.

There are many risks involved with advancing instruments over a guidewire. For example, a catheter or other instrument may skive or otherwise damage a wall of a vessel, particularly as the instrument passes through narrow passages or tortuous anatomy involving sharp bends. Such instruments also risk dislodging embolic material or even perforating the vessel wall.

In addition, it is often desirable to access very small vessels deep within the body, e.g., within a patient's heart, for example, to place a ventricular pacing lead within a coronary vein. However, the instrument(s), e.g., guide sheath, lead, etc., may have a relatively large cross-section and/or may have a relatively blunt distal tip, making it difficult to advance such instruments as deeply as desired into such small vessels.

Further, it may be desirable to deliver diagnostic and/or therapeutic agents into cardiac tissue. For example, stem cells are a potentially therapeutic agent, which may be delivered to tissue, e.g., cardiac tissue to facilitate regeneration of myocardial cells in dead or damaged tissue, resulting from an infarction or other cardiac event. However, it may be difficult to deliver such agents into cardiac tissue, because of the difficulty in accessing such regions, particularly adjacent relatively small vessels. In addition, delivering agents into a vessel or other body lumen may result in migration and/or dilution of the agents, e.g., due to normal blood flow, which may impair efficacy of the agents.

Accordingly, apparatus and methods for delivering agents into cardiac or other tissue surrounding blood vessels or other body lumens would be useful.

SUMMARY OF THE INVENTION

The present invention is directed generally to apparatus and methods for delivering agents and/or instruments during a medical procedure. More particularly, the present invention is directed to apparatus and methods for delivering agents, e.g., therapeutic and/or diagnostic agents, such as stem cells, into tissue within a patient, e.g., within cardiac tissue surrounding one or more vessels, or other tissue surrounding body lumens, e.g., within the coronary, neuro, and/or peripheral vasculature, within the patient's gastrointestinal tract, urogenital tract, respiratory tract, lymphatic system, and/or within surgically created passages.

In accordance with one embodiment, a system is provided for accessing a body lumen that includes an expandable member including a lumen, and a source of one or more agents, e.g., one or more therapeutic and/or diagnostic agents, communicating with the lumen. The expandable member may include a proximal end, a distal end sized for introduction into a body lumen, and a lumen extending therebetween. At least a portion of the expandable member is expandable from a contracted condition to minimize a profile of the expandable member, e.g., to allow insertion into a target body lumen, and an enlarged condition wherein the expandable member may be relatively large compared to the body lumen to substantially seal the body lumen, e.g., to substantially isolate the body lumen from other normally connected body lumens. The source of agent(s) may be capable of delivering the agent(s) at sufficient pressure to cause the agent(s) to extravasate through the wall of the isolated body lumen and into the surrounding tissue when delivered from the expandable member lumen.

In one embodiment, the expandable member may be an expandable sheath having sufficient length such that the proximal end may remain outside the patient's body, while the distal end is disposed within a target body lumen being isolated. In another embodiment, the expandable member may include an expandable sheath extending from a nonexpandable elongate tubular member. In yet another embodiment, the expandable member may be a catheter or other tubular member including a balloon or other expandable member on its distal end.

In accordance with another embodiment, a method is provided for delivering one or more agents to tissue surrounding a target body lumen. A distal end of an elongate member may be advanced through one or more body lumens until the distal end is disposed within or adjacent the target body lumen. The target body lumen may be sealed using the distal end of the elongate member, thereby substantially isolating the target body lumen. One or more agents may be delivered into the target body lumen with sufficient pressure to extravasate the one or more agents into tissue surrounding the target body lumen.

In accordance with still another embodiment, a method is provided for delivering stem cells to cardiac tissue surrounding a cardiac vessel. A target body lumen, e.g., a coronary vein, may be accessed, substantially isolated, and inflated with fluid including the stem cells with sufficient pressure to extravasate the stem cells into the surrounding cardiac tissue. Thus, localized delivery of stem cells or other agents may be achieved, thereby minimizing the amount of stem cells (or other agents) required to achieve a desired therapy.

In accordance with yet another embodiment, a method is provided for delivering one or more agents into cardiac tissue. A distal end of an elongate delivery device may be introduced into one or more lumens of the heart, e.g., via the coronary sinus, until the distal end is within or adjacent the target vessel. At least the distal end may be expanded to substantially isolate the target vessel, and fluid may be delivered via the delivery device into the target vessel with sufficient pressure to extravasate the fluid into tissue surrounding the target vessel.

In accordance with still another embodiment, a method is provided for delivering an instrument into a branch body lumen from a main body lumen within a patient's body. A distal portion of a sheath apparatus may be advanced into the patient's body until a distal end of the sheath apparatus is disposed in the main body lumen adjacent the branch body lumen. An occlusion member on the distal end of the sheath apparatus may be expanded within the main body lumen.

Other aspects and features of the present invention will become apparent from consideration of the following description taken in conjunction with the accompanying drawings.

DETAILED DESCRIPTION OF THE PREFERRED EMBODIMENTS

Figure 1:
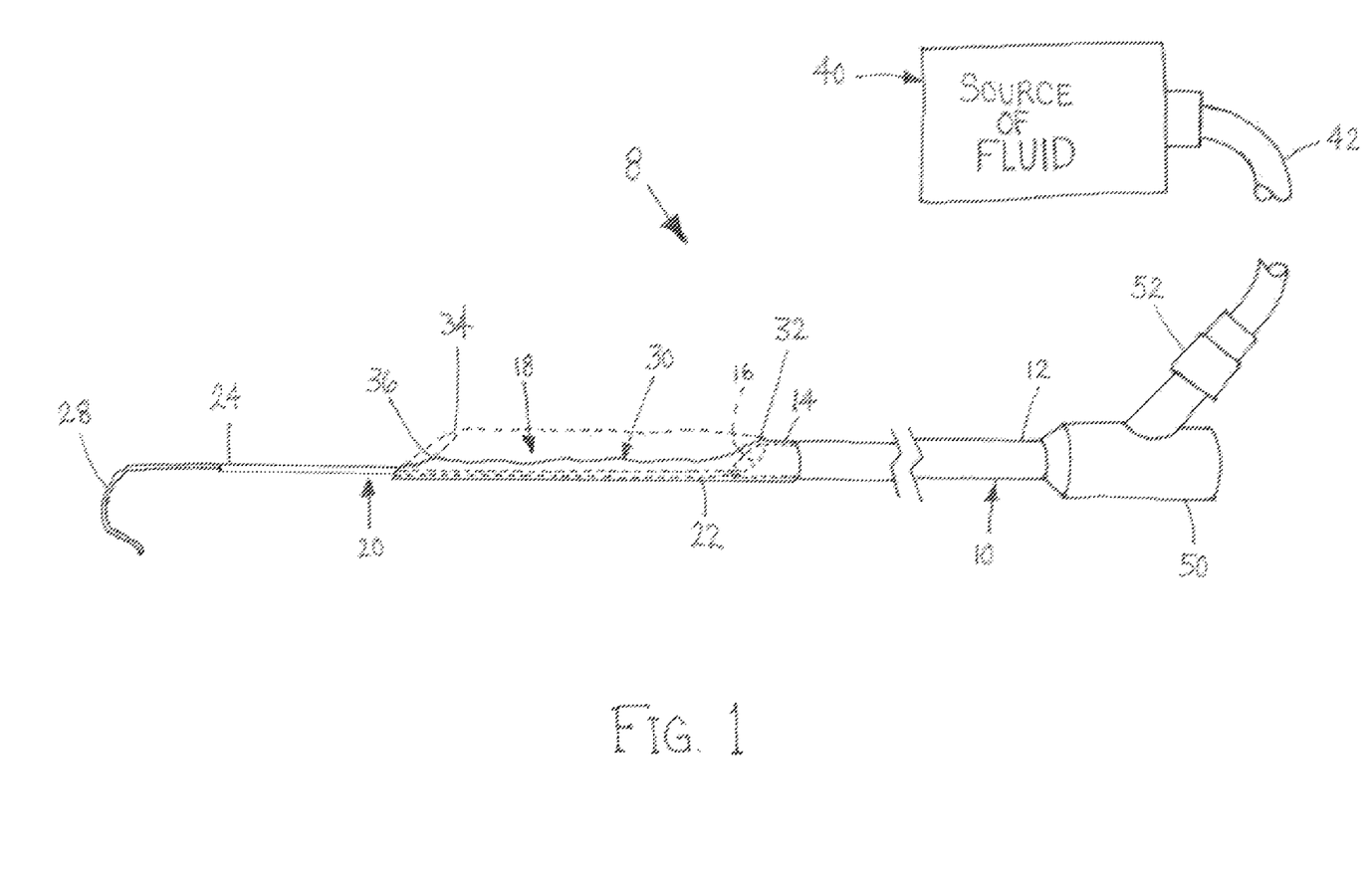
FIG. 1 is a side view of a first embodiment of a delivery apparatus, including a tubular proximal portion and an expandable distal portion.

Turning to the drawings, FIG. 1 shows a first embodiment of an apparatus 8 for delivering fluid and/or one or more agents to tissue surrounding a target body lumen (not shown) and/or for delivering one or more instruments (also not shown) within the body lumen. As explained further below, the target body lumen may be a vessel within a patient's vasculature, e.g., a coronary vessel adjacent infarcted tissue, a body lumen within the gastrointestinal tract, urogenital tract, respiratory tract, lymphatic system, and the like.

Generally, the apparatus 8 includes a tubular proximal portion 10, an expandable distal portion 18, and a source of fluid 40 including one or more agents. The tubular proximal portion 10 is an elongate tubular member, e.g., a catheter, sheath, and the like, including a proximal end 12, a distal end 14 sized for insertion into a body lumen, and a lumen 16 extending between the proximal and distal ends 12, 14. Optionally, the tubular proximal portion 10 may include one or more additional lumens (not shown), e.g., for receiving a guidewire, inflation media, and/or for perfusion, as described further below. Such additional lumens may be disposed concentrically around one another or in a side-by-side arrangement.

The wall of the tubular portion 10 may be sufficiently thick such that the diameter (or other peripheral dimension) of the tubular portion 10 remains substantially fixed during use of the apparatus 8. The wall of the tubular portion 10 may be rigid or flexible, although self-supporting such that the tubular portion 10 does not collapse on itself. The tubular portion 10 may be sufficiently flexible to allow the tubular portion 10 to bend or otherwise be advanced through a patient's vasculature, while minimizing the risk of kinking or buckling.

The tubular portion 10 may have uniform or variable flexibility material along its length between the proximal and distal ends 12, 14, as desired. For example, it may be desirable for the proximal end 12 to be substantially rigid or semi-rigid, e.g., to facilitate advancing or pushing the apparatus 8, while the distal end 14 may be semi-rigid or substantially flexible to accommodate advancement through tortuous anatomy within a patient's vasculature.

The tubular portion 10 may be formed from a variety of materials, such as PTFE, FEP, PFA, PE, Polyamides (Nylon), Polyimide, Pebax, Urethane, and the like. Optionally, the tubular portion 10 may include one or more braids or coils, e.g., embedded within the wall, to provide reinforcement for the tubular portion. In exemplary embodiments, the tubular portion 10 may have a diameter between about half and five millimeters (0.5-5 mm), a wall thickness between about 0.02 and one millimeters (0.02-1.0 mm) (cross-sectional configurations, i.e. multi-lumen cross-sections, and the like may cause wall thicknesses to vary), and a length between about ten and one hundred ten centimeters (10-110 cm).

For example, if a subclavian approach to the heart is to be used, the proximal portion 10 may have a length of about thirty centimeters (30 cm) or less, while if a femoral approach is to be used, the proximal portion 10 may have a length of about one hundred ten centimeters (110 cm) or more. In one embodiment, the tubular portion 10 may have a length sufficient to reach the vena cava, the right atrium, or the coronary sinus of a patient's heart from a percutaneous entry location, such as a subclavian or femoral vein.

With continued reference to FIG. 1, the expandable distal portion 18 generally includes an elongate stiffening member 20 providing a "backbone" for the distal portion 18 and an expandable sheath 30. The stiffening member 20 and/or expandable sheath 30 may be attached to or otherwise extend distally from the distal end 14 of the tubular portion 10. The stiffening member 20 facilitates advancing the expandable sheath 30 through one or more body lumens, e.g., through a patient's vasculature. The distal portion 18 may be similar in construction and use as the apparatus disclosed in application Ser. No. 10/423,321, filed Apr. 24, 2003, the entire disclosure of which is expressly incorporated by reference herein. In addition or alternatively, the distal portion 18 may be constructed using materials and/or methods similar to any of the embodiments described in applications Ser. Nos. 10/958,034, filed Oct. 4, 2004, and Ser. No. 11/347,361, filed Feb. 3, 2006, the entire disclosures of which are expressly incorporated by reference herein.

The stiffening member 20 may be a solid or hollow guidewire, catheter, thread or other filament (e.g., a monofilament), and/or other solid or hollow elongate member. The stiffening member 20 may be sufficiently flexible to facilitate advancement through tortuous anatomy without causing dissection or perforation, yet may have sufficient column strength and/or torque-ability to be "pushable," i.e., such that the stiffening member 20 may be advanced through a body lumen by pushing the proximal end 12 of the tubular portion 10 without substantial risk of kinking and/or buckling. In addition, the stiffening member 20 may also provide sufficient support to facilitate introducing secondary devices, such as a cardiac lead, through the distal portion 18. Cardiac leads or other floppy devices may be difficult to deliver, because of their ability to "prolapse" or double over on themselves in large lumens, like atria, rather than advance to a desired proper location.

In addition, the stiffening member 20 may have sufficient length to be advanced from a first location where the proximal portion 12 terminates, e.g., within the right atrium or coronary sinus of a heart, and a site to be accessed and/or treated, e.g., a coronary vein, as described further below. In exemplary embodiments where the stiffening member 20 is attached to the distal end 14 of the proximal portion 10, the stiffening member 20 may be between about three and fifty centimeters (3-50 cm), or may be not more than about thirty centimeters (30 cm). Alternatively, the stiffening member 20 may extend proximally the entire length of the proximal portion 10, e.g., within or along the proximal portion 10, and therefore may have additional length corresponding to the length of the proximal portion 10.

As shown in FIG. 1, the stiffening member 20 may be an elongate member including a proximal end 22, and a distal end 24 having a size and/or shape for insertion into a body lumen. Optionally, the stiffening member 20 may terminate in a rounded or other substantially atraumatic distal tip 28, e.g., a "J" tip, a balloon or other expandable member (not shown), and the like. If desired, the distal tip 28 may be shaped to provide steerability and/or directionality, or may include one or more internal elements to provide a steerable distal tip, as described in application Ser. No. 11/347,361, incorporated by reference above. Optionally, the distal tip 28 may be formed from multiple sections of tubing or other material having different stiffness or modulus of elasticity (not shown), as disclosed in the applications incorporated by reference above.

Optionally, the stiffening member 20 may include one or more lumens (not shown) extending between the proximal and distal ends 22, 24. The lumen(s) may be sized to allow fluids to be delivered therethrough and/or to receive a guide wire, catheter, or other instrument (not shown) therethrough. The stiffening member 20 may have a cylindrical or other substantially symmetrical cross-section, e.g., including a single lumen (not shown). Alternatively, the stiffening member 20 may have an asymmetrical cross-section, e.g., including a plurality of lumens (also not shown). In other embodiments, the stiffening member may have an arcuate cross-section (not shown), such as those disclosed in application Ser. No. 10/432,321, incorporated by reference above. The diameter or other cross-section of the stiffening member 20 is substantially smaller than that of the tubular proximal portion 10, e.g., between about 0.05-5 millimeters, or between about 0.2-2 millimeters.

Figure 4A:
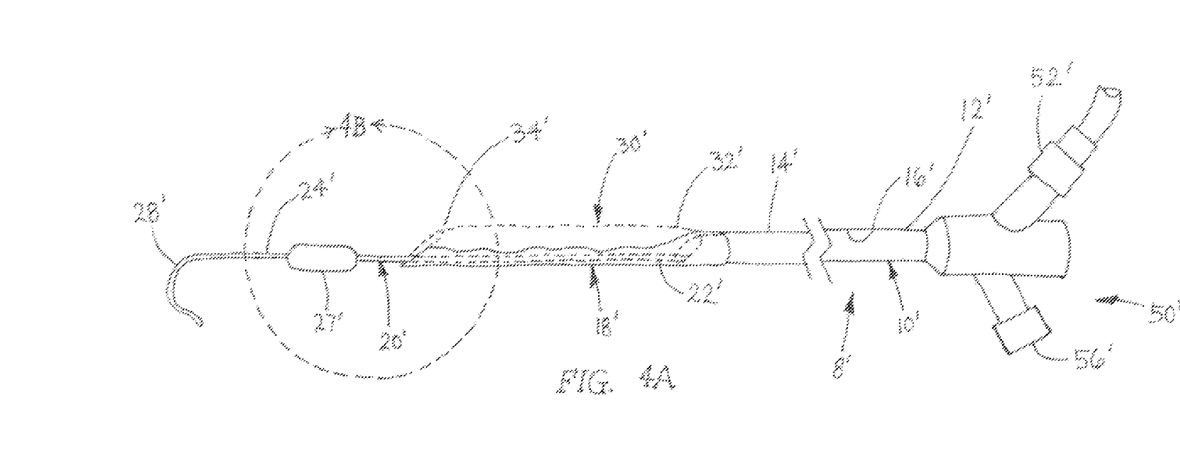
FIG. 4A is a side view of another embodiment of a sheath apparatus, including a tubular proximal portion and an expandable distal portion.
Figure 4B:
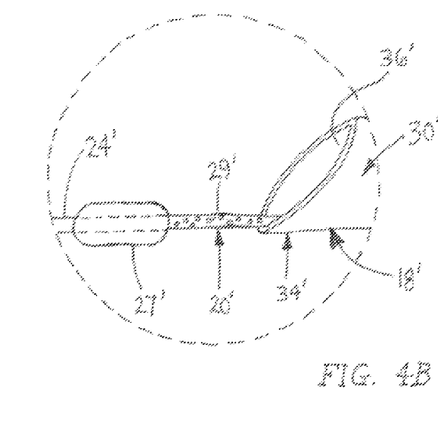
FIG. 4B is a detail of the apparatus of FIG. 4A.

Optionally, as best seen in FIGS. 4A and 4B, the stiffening member 20' may include a balloon or other expandable occlusion member 27' on the distal end 24.' If a balloon 27' is provided, the stiffening member 20' may include an inflation lumen (not shown) that extends through the stiffening member 20' from the proximal end 12' to communicate with an interior of the balloon 27.' A source of inflation media, e.g., a syringe of saline (not shown) may be coupled to port 56' that may communicate with the inflation lumen. Exemplary occlusion members that may be provided and methods for using them are disclosed in co-pending application Ser. No. 10/934,082, filed Sep. 2, 2004, the entire disclosure of which is expressly incorporated by reference herein.

In addition or alternatively, with particular reference to FIG. 4B, the stiffening member 20' may include one or more openings/outlet ports 29' on the distal end 24,' e.g., distal or proximal to the balloon 27.' If the stiffening member 20' includes a balloon 27' and one or more outlet ports 29,' the stiffening member 20' may include two lumens (not shown) communicating with the interior of the balloon 27' and the outlet ports 29,' respectively.

The stiffening member 20, 20' may be formed from a variety of materials and using various methods. For example, the stiffening member may be formed from plastic, glass, metal, or composites of such materials using known methods, such as extrusion and the like, thereby providing a desired combination of flexibility and column strength. In exemplary embodiments, the stiffening member may be formed from one or more of polyimide, polyamide (nylon), Ultem, PEEK, Nitinol, and optionally, may include braid and/or coil reinforcing polymers.

Returning to FIG. 1, a transition may be provided between the distal end 14 of the tubular portion 10 and the proximal end 22 of the stiffening member 20. As shown, the distal end 14 of the tubular portion 10 may be beveled or otherwise tapered, e.g., by molding-in the tapered shape or by cutting or otherwise removing a section of the distal end 14. Such a shape may facilitate advancing the tubular portion 10 into a body lumen within which the smaller stiffening member 20 has been previously introduced, as described further below.

In addition or alternatively, an obturator (not shown) may be provided that is sized to be slidably inserted into the lumen 26 of the tubular portion 10. The obturator may have a length corresponding to a length of the tubular portion 10 such that the obturator extends partially into the expandable distal portion 18 when the obturator is fully advanced into the tubular portion 10. The obturator may be relatively flexible and/or soft to provide an atraumatic transition between the tubular proximal portion 10 and the expandable distal portion 18.

Returning to FIG. 1, the proximal end 22 of the stiffening member 20 may be attached to the distal end 14 of the tubular portion 10, e.g., such that the stiffening member extends axially and/or tangentially from the wall of the tubular portion 10. The stiffening member 20 may be attached to the tubular portion 10, e.g., by one or more of chemical bonding, thermal bonding, sonic welding, interference fit, and/or one or more cooperating connectors. Alternatively, the tubular portion 10 and stiffening member 20 may be formed as a single piece, e.g., by extrusion, injection molding, and the like.

With continued reference to FIG. 1, the expandable sheath 30 generally includes a proximal end 32, a distal end 34, and one or more side walls extending between the proximal and distal ends 32, 34, thereby at least partially defining a lumen 36. As used herein, the term "sheath" may include any structure that at least partially defines a lumen, whether the structure is substantially tubular or only partially defines the lumen 36.

As shown in FIG. 1, the sheath 30 may be expandable from a contracted condition (shown in solid) to an enlarged condition (shown in phantom). When the sheath 30 is in the contracted condition, the distal portion 18 may assume a low profile to facilitate insertion into a body lumen (not shown). To place the sheath 30 in the contracted condition, the sheath 30 may be folded, twisted, wrapped, or otherwise compressed around or adjacent to the stiffening member 20 (e.g., using an internal vacuum with the lumen 36 of the sheath 30 and/or an external force). In another embodiment, the sheath 30 may be left unconstrained. The "limpness" of the sheath 30 may allow the sheath material to readily deflect when the sheath 30 contacts any bodily structures, such that the sheath 30 may perform as if it were maintained in a collapsed configuration, when it is not actually constrained.

Optionally, the sheath 30 may be secured in the contracted condition, e.g., using a constraint (not shown), such as a sheath, tether, or releasable adhesive or bonding material at one or more locations or continuously along the sheath 30. Alternatively, the sheath 30 may simply maintain the contracted condition until an external force, e.g., fluid or an instrument, are delivered therein to expand the sheath 30 towards the enlarged condition. Exemplary apparatus and methods for placing and/or maintaining the sheath 30 in the contracted condition are disclosed in application Ser. No. 10/423,321, incorporated by reference above.

In the enlarged condition, the sheath 30 may unfold, untwist, unwrap, or otherwise expand to at least partially define the lumen 36, e.g., for receiving a fluid (e.g., a medicament, anti-thrombotic agent, and the like) and/or one or more instruments therethrough (not shown).

Because the sheath 30 is relatively thin-walled, the distal portion 18 may attain a relatively low profile when the sheath 30 is in the contracted condition compared to the proximal portion 10. For example, with the sheath 30 in the contracted condition, the distal portion 18 may have a maximum diameter between about 0.1 and about ten millimeters (0.1-10 mm), or between about 0.2 and about three millimeters (0.2-3 mm). Conversely, a relatively large lumen 36 may be provided when the sheath 30 is expanded to the enlarged condition. For example, the lumen 36 may have a diameter or other maximum cross-section between about 0.3 and about one hundred millimeters (0.3-100 mm), or between about 0.3 and about twenty millimeters (0.3-20 mm).

The sheath 30 may be formed from relatively thin, flexible material, as compared to the stiffening member 20 and/or tubular proximal portion 10. Thus, the sheath 30 may be "flimsy," i.e., may have little or no rigidity such that the sheath 30 provides little resistance to expansion and/or contraction, and/or may conform substantially to anatomy within which it is deployed. As used herein, "flimsy" means that the material of the sheath 30 is not biased to assume any particular configuration or shape, and therefore, the sheath 30 may adopt whatever shape and/or configuration that is imposed upon it, e.g., by being folded or otherwise compressed, by being subjected to external or internal pressure or force, and the like. To achieve this, the sheath 30 may have a relatively thin wall thickness, e.g., between about 0.001-1.25 millimeters, or between about 0.005-0.06 millimeter.

The sheath 30 may be constructed of one or more materials, e.g., polytetrafluoroethylene (PTFE), expanded polytetrafluoroethylene (ePTFE), fluorinated ethylenepropylene (FEP), polyethylene teraphathalate (PET), urethane, olefins, polyethylene (PE), silicone, latex, isoprene, chronoprene; and the like. The sheath 30 may be formed from lubricious material and/or may be coated, e.g., with silicone or other coating, e.g., for facilitating inserting one or more instruments (not shown) through the lumen 36.

In some embodiments, this may be accomplished by forming the sheath 30 out of a lubricious material such as, a hydrophobic fluoropolymer. Alternatively, the sheath 30 may be formed from material that has been surface-treated and/or coated with a hydrophilic coating material. If it is particularly difficult to treat or coat the interior surface of the sheath 30, the treatment or coating material may be applied to the exterior surface of the sheath 30. The sheath 30 may then be inverted or "everted," for example, by pulling one end of the sheath 30 through the sheath lumen to place the exterior treated/coated surface on the interior of the sheath 30 (i.e., turn the sheath 30 inside-out).

The sheath 30 may be formed from thin-walled polymeric tubing or a thin polymeric film. With respect to tube-based structures, the tubing may be extruded (or co-extruded if multiple lumens are used as is described in more detail below) to a thin wall. Alternatively, one or more post-processing steps, such as blow molding, stretching, or drawing tube through a heated die may be used to form the thin walled sheath 30. In still another embodiment, a thin film may be produced and rolled into a tubular configuration. In this embodiment, the thin film may be surface-treated and/or coated before being rolled into the tubular configuration.

With respect to thin film-based structures, a seam may be formed along all or a portion of the length of the sheath 30. The seam may be formed from any number of methods, for example, chemical bonding with adhesives, heat sealing, ultrasonic welding, laser welding, or mechanical bonding using stitching or the like.

As described above, in one embodiment, the sheath 30 may be formed from a lubricious fluoropolymer. For example, a thin-walled sheath 30 may be formed by rolling a cast thin film formed from PTFE having a layer of FEP formed thereon into a tubular structure. The FEP may then be sealed (for example, by heat sealing) to form the final tubular structure. The PTFE layer may be disposed on the interior surface of the sheath 30 since PTFE is more lubricious than FEP.

In still another alternative embodiment, the sheath 30 may be formed from ePTFE manufactured into a thin-walled tube (or multiple tubes) or thin film. Additional lumens may also be formed within the sheath 30. For example, these additional lumens may be used to house the backbone (i.e., elongate stiffening member 20) or used to inject contrast for imaging and/or perfusing blood or other fluids. As one example, additional lumens may be formed by joining un-sintered PTFE or ePTFE tube structures, which may then be heat-sealed along their lengths, followed by a sintering process.

In one embodiment, the sheath 30 is formed from substantially inelastic material, i.e., such that a primary contribution to the sheath 30 expanding and contracting is unfolding or folding the material of the sheath 30. Alternatively, the sheath 30 may be formed from an elastic material such that a secondary contribution to the sheath 30 expanding and contracting is an elasticity of the material of the sheath 30, i.e., such that a circumference or other peripheral dimension of the sheath 30 may increase as the sheath 30 expands towards the enlarged condition.

The sheath 30 may be substantially nonporous. Alternatively, the sheath 30 may be porous, for example, substantially continuously along its length or at one or more locations, e.g., to allow fluid delivered into the lumen 36 to pass through the wall of the sheath 30 in a desired manner, e.g., to deliver fluid to a wall of a vessel (not shown) through which the sheath 30 extends. In a further alternative, the sheath 30 may include one or more discrete openings (not shown) at one or more locations along its length, e.g., at the distal end 34.

In addition or alternatively, the sheath 30 may include a thin mesh, e.g. a perforated urethane film and the like. In a further alternative, the lubricity of the sheath 30 may be enhanced by providing a lubricious coating, lining, ribbing, and the like (not shown), and/or applying a lubricant, e.g., to the interior surface and/or outer surface of the sheath 30. The sheath 30 may include a single layer or multiple layers of such materials, such that a desired flexibility and lubricity is achieved. Thus, the sheath 30 may easily expand and/or line a body lumen to reduce friction and/or accommodate instruments being advanced through the body lumen, as explained further below.

Optionally, the sheath 30 may include one or more reinforcing elements (not shown). For example, one or more wires, threads, filaments, and the like, formed from plastic, glass, metal, or composites of such materials, may be attached to an outer surface, an inner surface, and/or embedded in a wall of the sheath 30. In addition or alternatively, the sheath 30 may include relatively thickened regions that may be formed directly from the wall material. The reinforcing element(s) may extend circumferentially and/or helically around the sheath 30, and/or may extend axially along the sheath 30, depending upon the reinforcement desired. The reinforcement element(s) may also bias the sheath 30 to assume a desired shape or configuration when expanded towards the enlarged condition.

With continued reference to FIG. 1, the proximal end 32 of the sheath 30 may be attached to the distal end 14 of the tubular portion 10, e.g., by chemical bonding, thermal bonding, sonic welding, interference fit, and the like. Thus, as shown, the sheath 30 may surround and overly the distal end 14 of the tubular portion 10 such that the lumen 16 of the tubular portion 10 communicates with the lumen 36 of the sheath 30. When the sheath 30 is compressed to the contracted condition, the proximal end 32 of the sheath 30 may be compressed against the tapered distal end 14 of the tubular portion 10. Alternatively, other constructions may be possible, such as those disclosed in the applications incorporated by reference above.

Returning to FIG. 1, optionally, a proximal end 12 of the tubular proximal portion 10 may include a handle or other structure 50, e.g., that may facilitate manipulating the apparatus 8 and/or inserting one or more instruments into the lumen 16 of the tubular portion 10. In addition or alternatively, the handle 50 may include one or more ports and/or valves, e.g., side port 52 communicating with the lumen 16. In addition, the handle 50 may include one or more additional ports (not shown) for communicating with respective one or more lumens within stiffening member 20.

As shown in FIG. 1, a source of fluid 40 is coupled to the side port 52, e.g., using tubing 42. The tubing 42, side port 52, and/or source of fluid 40 may include luer lock or other connectors for detachably coupling the source of fluid 40 to the side port 52. Alternatively, the source of fluid 40 may be substantially permanently coupled to the side port 52.

The source of fluid 40 may include any device capable of delivering fluid through the lumens 16, 36 with sufficient pressure to cause extravasation of the fluid through the wall of a vessel communicating with the lumens 16, 36, as explained further below. The source of fluid 40 may be a manual device or an automated device. For example, the source of fluid 40 may simply be a syringe (not shown) including a barrel containing the fluid and a piston and/or plunger (also not shown) that may be depressed into the barrel to deliver the fluid out of the syringe, through the tubing 42. The barrel may include sufficient volume of the fluid to expand the sheath 30 and fill a target vessel with sufficient fluid to expose the target vessel to sufficient internal pressure to cause extravasation.

Alternatively, the source of fluid 40 may be a pump (not shown), capable of delivering a continuous flow rate or predetermined volume of fluid through the lumens 16, 36 into a target vessel. The pump may include one or more settings, e.g., a first setting intended to deliver a desired flow rate or volume into the lumens 16, 36 until a predetermined threshold pressure is achieved, and a second higher setting where the threshold pressure is exceeded to cause extravasation, as explained further below.

The source of fluid 40 may include one or more agents, e.g., dissolved, suspended, or otherwise carried by the fluid. For example, the one or more agents may include stem cells, genes, proteins, small molecules, cellular and other growth factors, and the like. The fluid may be any liquid or gas capable of sufficiently inflating the sheath 30 and/or pressurizing the target vessel, e.g., water, saline, carbon dioxide, and the like. Alternatively, a separate source of agent(s) (not shown) may be provided that is coupled to a port (also not shown) on the handle 50. The source of agent(s) may be independently deliverable through the apparatus 8, e.g., through the same lumen as or a separate from the source of fluid 40. Alternatively, the source of fluid may be capable of adding one or more agents to the fluid after initially delivering fluid without such agent(s).

During use, an expandable apparatus, such as apparatus 8 shown in FIG. 1 and described above (or other apparatus described herein), may be used to deliver fluid into a target vessel or other body lumen within a patient's body, e.g., a coronary vein, to cause extravasation and/or penetration of the fluid into tissue surrounding or otherwise adjacent the target vessel. It will be appreciated that the sheath apparatus described herein may also be used to provide access to a variety of body lumens, e.g., to perform diagnostic and/or therapeutic procedures, such as those disclosed in the applications incorporated by reference above.

Figure 2:
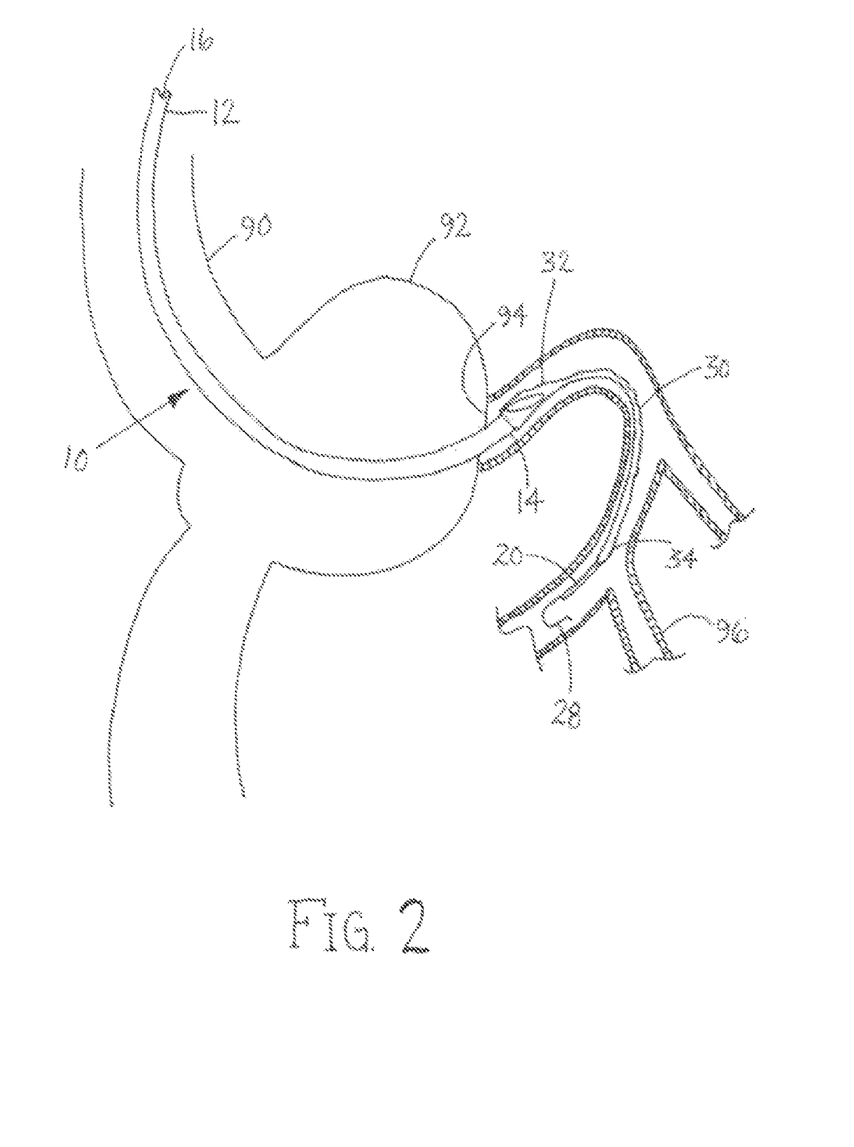
FIG. 2 is a cross-sectional view of a portion of a heart, showing the apparatus of FIG. 1 being delivered through the right atrium and into the coronary sinus of the heart.

Turning to FIGS. 2 and 3A-3E, an exemplary method is shown for using a sheath apparatus 8 (or any of the other apparatus described herein) to access and/or deliver one or more agents into tissue within a heart. FIG. 2 shows a portion of a heart, including a superior vena cava 90, right atrium 92, and coronary sinus 94, which communicates with the coronary venous system. As shown, the apparatus 8 may be used to deliver fluid, possible including one or more agents (not shown in FIG. 2), into a target vessel, e.g., coronary vein 96, and/or into tissue surrounding the target vessel 96.

Initially, the apparatus 8 may be provided with the sheath 30 constrained, collapsed, or otherwise unexpanded in the contracted condition. The apparatus 8 may be introduced into the patient's vasculature from a percutaneous entry site, e.g., a femoral vein or subclavian vein (not shown), using known methods and devices. The apparatus 8 may be advanced through the patient's venous system into the vena cava 90, the right atrium 92 of the heart, and finally into the coronary sinus 94 to reach the target coronary vein 96.

Fluoroscopy and/or other external imaging may be used to facilitate positioning the apparatus 8. Optionally, the apparatus 8 may include one or more radiopaque markers (not shown), e.g., on the distal end 24 of the stiffening member 20, the distal end 34 of the sheath 30, and/or the distal end 14 of the proximal tubular portion 10, to facilitate such imaging. In addition or alternatively, contrast may be introduced into the vein, e.g., via a fluid lumen in the stiffening member 20 of the apparatus 8 and/or through the lumen 34 (or other lumen, not shown) of the sheath 30, to facilitate fluoroscopic imaging. Such imaging may be used to identify the location of the sheath 30 relative to nearby structures, e.g., to ensure that the apparatus 8 is advanced as close as possible to a target extravascular location.

The apparatus 8 may be advanced through the patient's vasculature over a guidewire or other rail (not shown), e.g., by placing the guidewire along the desired path from the entry site to the target vessel 96 using conventional methods. For example, the guidewire may be backloaded through a guidewire lumen (not shown) of the stiffening member 20, and then the apparatus 8 may be advanced over the guidewire. Exemplary apparatus and methods for accessing the target vessel 96 to deliver the apparatus 8 are disclosed in applications Ser. Nos. 10/447,526, filed May 29, 2003, now U.S. Pat. No. 6,979,290, and Ser. No. 11/062,074, filed Feb. 17, 2005, the entire disclosures of which are expressly incorporated by reference herein.

Because of the relatively low profile of the expandable distal portion 18 with the sheath 30 collapsed (which is substantially the size of the stiffening member 20), the apparatus 8 may be able to access smaller coronary veins or be advanced further into a target coronary vein or other vessel than the tubular proximal portion 10 or conventional access sheaths.

Figure 3A:
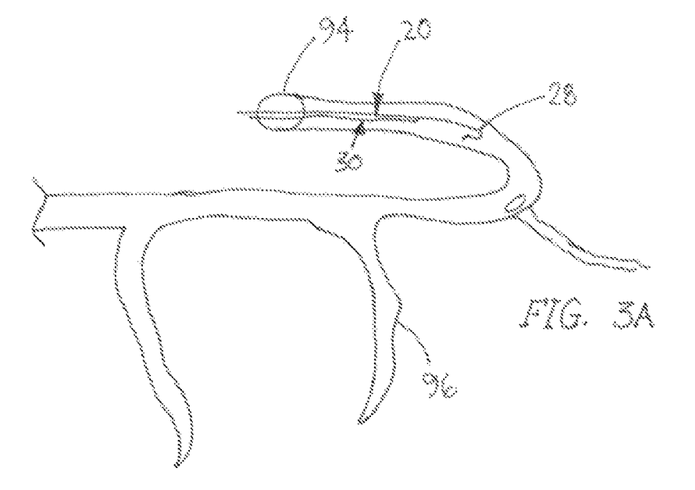
FIGS. 3A-3E are cross-sectional details of the heart of FIG. 2, showing the apparatus being used to isolate a target vessel and deliver fluid into the isolated vein with sufficient pressure cause extravasation of the fluid into tissue surrounding the isolated target vessel.
Figure 3B:
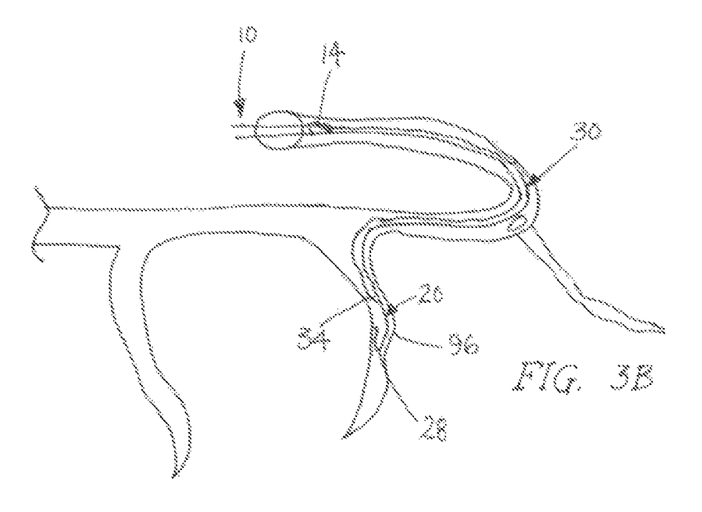

Turning to FIG. 3A, the distal tip 28 of the stiffening member 20 may be directed into the coronary sinus 94, and advanced or otherwise manipulated until the distal tip 28 is disposed within the target vessel 96, as shown in FIG. 3B. In FIG. 3B, the distal end 34 of the sheath 30 is disposed within the target vessel 96. Alternatively, the distal end 34 of the sheath 30 may be disposed within the ostium or otherwise adjacent the target vessel 96. When the distal end 34 of the sheath 30 is properly positioned, the distal end 14 of the tubular member 10 may be disposed within the coronary sinus 94, as shown, or outside the coronary sinus 94, i.e., within the right atrium 92 (not shown), if desired.

Figure 3C:
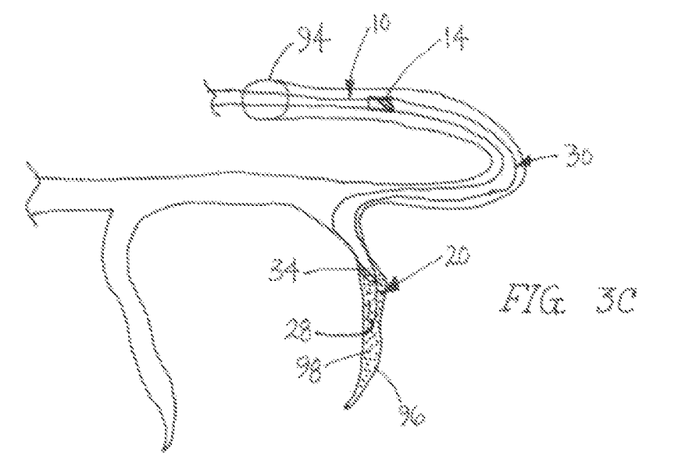

Turning to FIG. 3C, with the distal end 34 of the sheath 30 positioned within or adjacent the target vessel 96, fluid may be delivered through the apparatus 8 to inflate or otherwise expand the sheath 30 to substantially isolate the target vessel 96. For example, with additional reference to FIG. 1, the source of fluid 40 may be actuated or otherwise activated to deliver fluid through the lumens 16, 36, and out the distal end 34 of the sheath 30 into the target vessel 96.

As the distal end 34 of the sheath 30 expands, it may engage the wall of the target vessel 96, thereby substantially sealing the target vessel 96 from other nearby or connected vessels. For example, the sheath 34 may have a cross-section when expanded that is substantially equal to or greater than the target vessel 96. Thus, as the sheath 34 is expanded, it may exert an outward pressure against the wall of the target vessel 96 to provide a substantially fluid-tight seal. Furthermore, the expanded cross-section may be sized deliberately to seal within vessels of a desired diameter.

With the target vessel 96 substantially sealed, only a finite amount of fluid may be necessary to fill the target vessel 96 with fluid 98, as shown in FIG. 3C. If the source of fluid 40 is a syringe or other manual device, the medical operator may depress the plunger of the syringe to deliver a volume of fluid through the sheath 30 and into the target vessel 96 until resistance is detected, e.g., tactilely. For example, if an incompressible fluid is used, once the sheath 30 and the isolated target vessel 96 are substantially filled, the operator may feel tactile resistance to further delivery of the fluid 98. If the source of fluid 40 is a pump or other automatic device, the device may deliver fluid continuously or intermittently until a predetermined pressure level is reached, thereby indicating that the sheath 30 and the isolated target vessel 96 are substantially filled. For example, within the coronary veins, a pressure within the target vessel 96 of up to about one pound per square inch (1 psi) may be a threshold that may be set for the device to correspond to filling the target vessel 96.

Figure 3D:
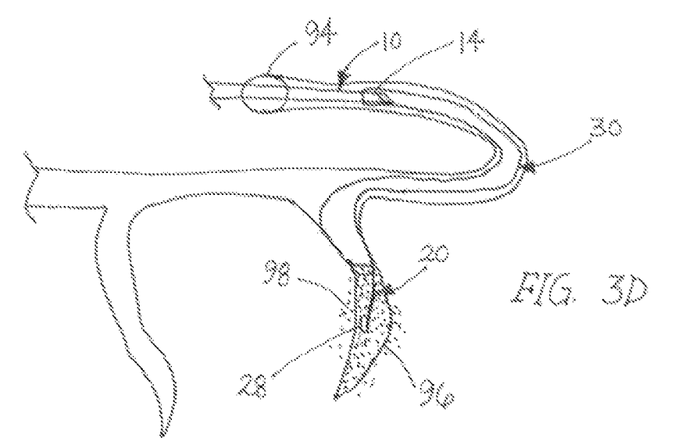

Turning to FIG. 3D, an additional volume of fluid may then be delivered through the apparatus 8, e.g., through the sheath 30 and into the target vessel 96 with sufficient pressure to cause extravasation of the vessel and force the fluid 98 to seep, permeate, or otherwise penetrate into tissue surrounding the target vessel 96, as shown in FIG. 3D. For example, pressure of at least about 0.2 pounds per square inch (psi), or between about 0.2 and fifteen pounds per square inch (0.2-15 psi) may cause local extravasation. As a result, the wall of the target vessel 96 may become porous, allowing the fluid 98 to be forced through the wall and into the surrounding tissue. In addition, the target vessel 96 may expand at least partially when the additional fluid is delivered.

The additional fluid may be delivered from the source of fluid 40, e.g., through the lumens 16, 36 of the apparatus 8, similar to the initial volume of fluid. Alternatively, agents may be delivered from a separate source, e.g., communicating with the lumens 16, 36, with another lumen in the sheath 30, e.g., along its wall, or with a lumen in the stiffening member 20.

Additional various fluids or agents that enhance or modulate permeability of vascular walls or other body lumens may be used in conjunction with delivery of stem cells and other agents, as described herein.

The additional fluid may be delivered manually, e.g., by depressing the plunger to overcome the resistance to further depression. For a pump, the pump may be capable of delivering fluid continuously or intermittently at a second higher pressure, e.g., as just described. For example, the pump may communicate with a separate reservoir including the one or more agents that the pump may deliver only during the second delivery.

Figure 3E:
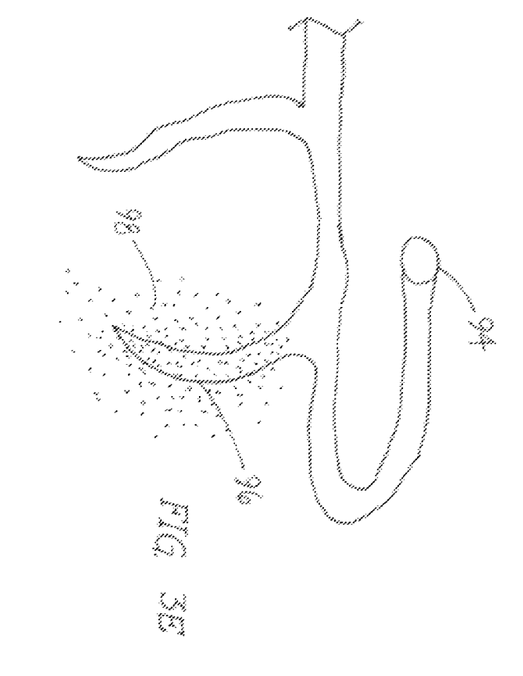

Turning to FIG. 3E, once sufficient fluid 98 (and agent(s)) has been delivered to tissue surrounding the target vessel 96, the apparatus 8 may be removed. For example, at least some of the fluid may be evacuated back through the sheath 30, which may cause the sheath 30 to collapse at least slightly, thereby unsealing the target vessel 96. Alternatively, it may be sufficient to simply reduce the pressure of the fluid through the sheath 30 to break the seal and allow the fluid 96 remaining within the target vessel 96 to flow away under substantially normal conditions.

Optionally, the distal end 34 of the sheath 30 may include one or more or a plurality of openings (not shown) disposed around the distal end 34. Such openings may allow fluid delivered through the sheath 30 to be forced through the openings and into the surrounding wall of the target vessel 96.

Thus, the apparatus 8 and methods described may be used to deliver one or more agents into a relatively localized tissue region, e.g., surrounding an isolated target vessel. Such localized delivery may reduce the amount of the agent(s) that must be delivered, as compared to injection into the target vessel under conditions where the fluid is free to flow out of the target vessel. Thus, localized delivery may reduce the cost of delivering expensive agent(s), such as stem cells or other gene therapy materials, which may also be difficult to obtain. Localized delivery may also protect other nearby regions, e.g., which may be damaged or otherwise adversely affected upon exposure to certain agents.

As a particular example, stem cells may be delivered to infarcted tissue within the heart by using the apparatus 8 to access and substantially isolate a coronary vein or other vessel immediately adjacent the infarcted tissue, and delivering fluid carrying stem cells with sufficient pressure to extravasate the vessel and deliver the stem cells into the infarcted tissue.

Figure 5:
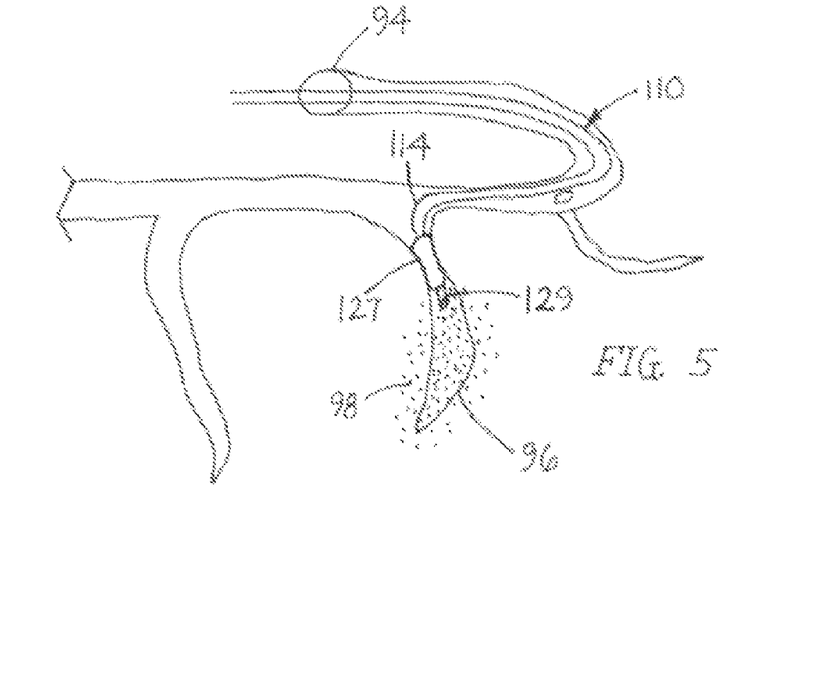
FIG. 5 is a cross-sectional detail of a patient's heart, showing another method for delivering fluid by extravasation into tissue surrounding an isolated target vessel within the heart.

In an alternative embodiment, shown in FIG. 5, a balloon catheter 110 may be used instead of the apparatus 8 to substantially isolate a target vessel 96 and deliver fluid with sufficient pressure to extravasate the fluid 98 (and one or more agents) into the surrounding tissue. As shown in FIG. 5, the catheter 110 may include a proximal end (not shown), a distal end 114 carrying a balloon or other expandable member 127, and an infusion lumen 116 communicating with one or more openings 129. As shown, the openings 129 may be distal to the expandable member 127, although, in some embodiments, it may be desirable to having one or more openings 129 proximal to the expandable member 127.

The catheter 190 may be delivered similar to the apparatus 8, e.g., by introducing the distal end 114 with the expandable member 127 collapsed. Once positioned within or adjacent the target vessel 96, the expandable member 127 may be expanded to substantially isolate the target vessel 96. Fluid 98 may then be delivered via the lumen 116 and opening(s) 127 into the target vessel 96 to extravasate and deliver the fluid and/or one or more agents into tissue surrounding the target vessel 96. One disadvantage of such a catheter, however, is that it may have a larger profile than the distal tip 28 of the apparatus 8, and therefore may not be able to access vessels that are as small as those accessible using the apparatus 8.

Turning to FIGS. 6A-6D, another method is shown for delivering a therapeutic agent 98 into a section of a target vessel 96, e.g., within the coronary venous system, similar to the apparatus 8 and methods described above. In this embodiment, with additional reference to FIG. 4, an apparatus 8' may be used that includes an expandable sheath 30' and a balloon or other expandable member 27' spaced apart from the distal end 34' of the sheath 30,' e.g., along the stiffening member 20.'

Figure 6A:
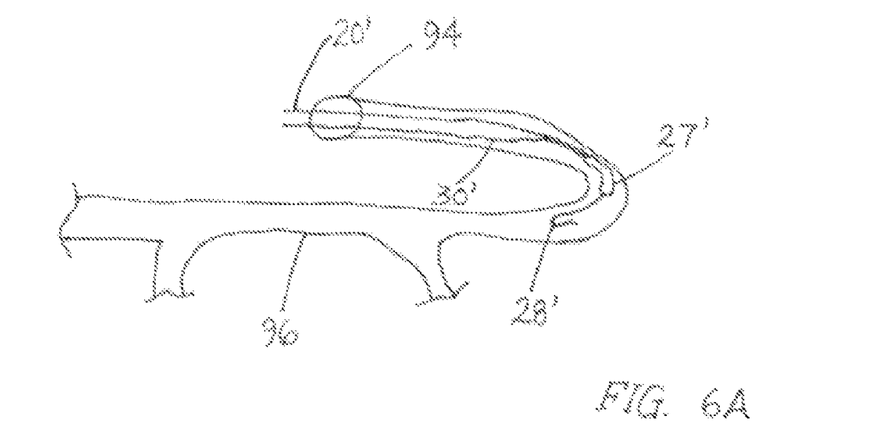
FIGS. 6A-6D are cross-sectional details of a patient's heart, showing a method for delivering a therapeutic agent into tissue surrounding a portion of a target vessel within the heart.
Figure 6B:
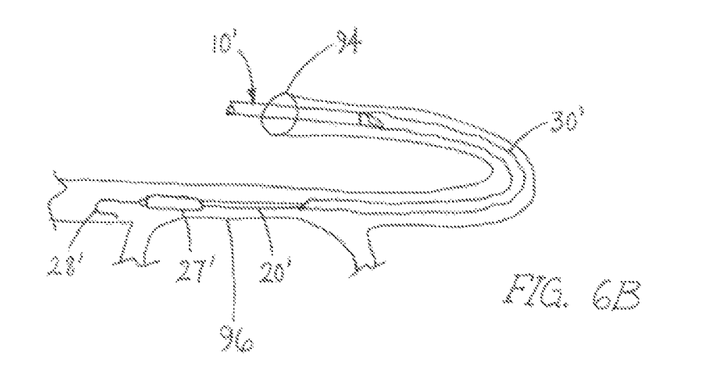

Initially, as shown in FIG. 6A, the apparatus 8' may be introduced through the coronary sinus 94 into the target vessel 96 with the expandable sheath 30' in its contracted condition and the balloon 27' collapsed. As shown in FIG. 6B, the apparatus 8' may be positioned within the target vessel 96 with the sheath 30' and balloon 27' disposed on opposite ends of a desired section of the target vessel 96.

Figure 6C:
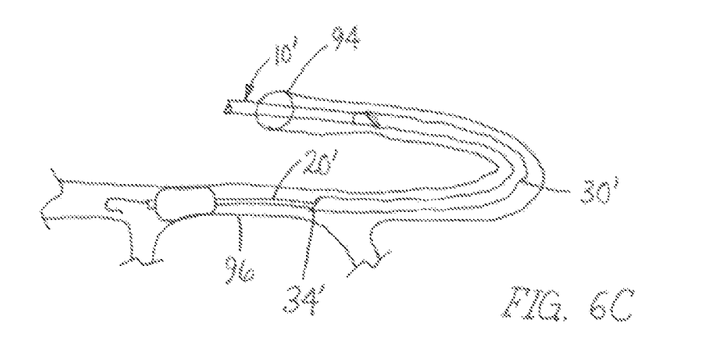

As shown in FIG. 6C, the balloon 27' may be expanded to at least partially occlude the target vessel 96, e.g., distal to the desired section. Fluid may then be delivered through the sheath 30,' similar to the previous embodiments, e.g., to expand the sheath 30' and substantially seal the target vessel 96, e.g., proximal to the desired section. Thus, the desired section of the target vessel 96 may be substantially isolated between the balloon 27' and the expanded sheath 30.'

Figure 6D:
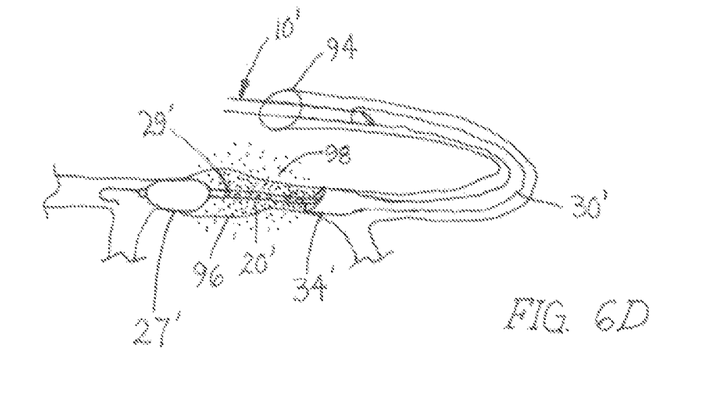

Turning to FIG. 6D, one or more agents may then be delivered into the isolated section and/or along with the fluid with sufficient pressure to cause extravasation through the wall of the isolated section. Thus, the agent(s) may be delivered locally to a distinct section of tissue surrounding a target vessel 96. Once sufficient agent(s) have been delivered, the sheath 30' and balloon 27' may be deflated or collapsed, and the apparatus 9' may be removed.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

We claim:

1. A system for delivering one or more agents to tissue surrounding a target vessel of a patient's body, the system comprising:
   an elongate delivery device comprising:
      a proximal tubular portion extending from a proximal end thereof to a distal end thereof over a length sufficient to reach a coronary sinus of the patient from a subclavian entry location, the distal end of the proximal tubular portion being tapered;
      a distal portion sized for introduction into the target vessel, the distal portion including an expandable sheath and a stiffening member, the expandable sheath including a proximal end, the proximal end of the sheath surrounding and overlying the distal end of the proximal tubular portion, being attached thereto, the expandable sheath extending from the proximal end thereof to a distal end thereof and the stiffening member including a proximal end, also being attached to the distal end of the proximal tubular portion, the stiffening member extending from the proximal end thereof to a distal end thereof and being attached to the expandable sheath, the distal end of the stiffening member being located distal to the distal end of the expandable sheath; and
   a lumen extending within the proximal tubular portion, between the proximal end of the tubular portion and the distal end of the tubular portion, and further extending distally, within the expandable sheath of the distal portion, to a distal opening of the lumen, which distal opening terminates the distal end of the expandable sheath; and
   a source of one or more agents coupled to the proximal end of the proximal tubular portion and communicating with the lumen in order to deliver the one or more agents through the lumen and out the distal opening thereof at a sufficient pressure to cause the one or more agents to extravasate through a wall of the target vessel, that is located downstream of the distal opening. and into surrounding tissue, when the distal portion of the device is introduced into the target vessel.

2. The system of claim 1, wherein the source comprises a device capable of delivering a fluid through the lumen and into the target vessel at a pressure of at least about 0.2 pounds per square inch (psi), at least a portion of the fluid containing the one or more agents.

3. The system of claim 1, wherein the stiffening member of the distal portion of the delivery device includes a lumen.

4. The system of claim 3, further comprising a guidewire sized for insertion within the lumen of the stiffening member.

5. A method for delivering one or more therapeutic agents to tissue surrounding a target vessel of a patient's body, the method comprising:
   advancing a distal portion of an apparatus into the target vessel, the distal portion including an expandable sheath, which is collapsed into a contracted condition while advancing the distal portion, the expandable sheath being attached to a distal end of a tubular portion of the apparatus and defining a lumen, the tubular portion including a lumen in fluid communication with the lumen of the expandable sheath; and
   delivering a volume of fluid, from at least one fluid source coupled to a proximal end of the tubular portion, through the lumen of the tubular portion, through the lumen of the expandable sheath, and out a distal end of the expandable sheath, the volume of fluid being sufficient to expand the expandable sheath and to fill the target vessel, immediately downstream of the distal end of the expandable sheath, and to apply a pressure sufficient to cause extravasation of the filled vessel;
   wherein the delivered volume of fluid comprises an initial volume and an additional volume;
   the initial volume of fluid is delivered to fill the vessel;
   the additional volume of fluid is delivered to apply the pressure sufficient to cause the extravasation of the filled vessel; and
   the additional volume includes the one or more therapeutic agents.

6. The method of claim 5, wherein:
   the at least one fluid source includes a first fluid source and a second fluid source;
   the initial volume of fluid is delivered from the first fluid source; and
   the additional volume of fluid is delivered from the second fluid source.

7. The method of claim 5, further comprising imaging the apparatus to facilitate advancing the apparatus into the target vessel.

8. The method of claim 5, wherein advancing the distal portion of the apparatus comprises advancing the apparatus over a guidewire, the guidewire having been inserted within a lumen of a stiffening member of the apparatus, the stiffening member extending alongside the expandable sheath and being attached to the distal end of the proximal tubular portion.

9. The method of claim 5, wherein:
the fluid source comprises a barrel containing the sufficient volume of fluid to cause the extravasation of the filled vessel; and
delivering the volume of fluid comprises moving a plunger within the barrel.

10. The method of claim 5, wherein in the one or more therapeutic agents are selected from the group consisting of: stem cells, genes, proteins, small molecules, cellular and other growth factors.

11. The method of claim 5, wherein at least one of the initial volume and the additional volume of fluid comprises an agent to modulate a permeability of the target vessel.

12. The method of claim 5, further comprising:
evacuating back, through the expandable sheath, a portion of the delivered volume of fluid in order to collapse the expandable sheath; and
removing the apparatus from the target vessel after evacuating the portion of the delivered volume of fluid.

13. A method for delivering one or more therapeutic agents to tissue surrounding a target vessel of a patient's body, the method comprising:
advancing an apparatus within the patient's body such that a distal end of a proximal tubular portion is located in proximity to a coronary sinus of the patient and a distal portion of the apparatus is located within the target vessel, the distal portion including an expandable sheath, which is collapsed into a contracted condition while advancing the apparatus, the expandable sheath being attached to the distal end of the proximal tubular portion of the apparatus and extending distally therefrom, the expandable sheath defining a lumen that extends from a lumen of the proximal tubular portion, being in fluid communication therewith; and
delivering a volume of fluid, from at least one fluid source coupled to a proximal end of the tubular portion, through the lumen of the tubular portion, through the lumen of the expandable sheath, and out a distal end of the expandable sheath into a portion of the target vessel, which is located downstream from the distal end of the expandable sheath, the volume of fluid being sufficient to expand the expandable sheath, to fill the portion of the target vessel, and to apply a pressure sufficient to cause extravasation of the filled portion of the target vessel;
wherein the delivered volume of fluid comprises an initial volume and an additional volume;
the initial volume of fluid is delivered to fill the portion of the target vessel;
the additional volume of fluid is delivered to apply the pressure sufficient to cause the extravasation of the filled portion of the target vessel; and
the additional volume includes the one or more therapeutic agents.

14. The method of claim 13, further comprising imaging the apparatus to facilitate advancing the apparatus into the target vessel.

15. The method of claim 13, wherein advancing the apparatus comprises advancing the apparatus over a guidewire, the guidewire having been inserted within a lumen of a stiffening member of the apparatus, the stiffening member extending alongside the expandable sheath and being attached to the distal end of the proximal tubular portion.

16. The method of claim 13, wherein:
the fluid source comprises a barrel containing the sufficient volume of fluid to cause the extravasation of the filled portion of the target vessel; and
delivering the volume of fluid comprises moving a plunger within the barrel.

17. The method of claim 13, wherein the fluid source comprises a pump capable of delivering a continuous flow rate of the fluid, and delivering the sufficient volume of fluid comprises setting a threshold pressure for the pump.

18. The method of claim 17, wherein the threshold pressure for the pump is in a range from approximately 0.2 psi to approximately 15 psi.

19. The method of claim 13, wherein in the one or more therapeutic agents are selected from the group consisting of stem cells, genes, proteins, small molecules, cellular and other growth factors.

20. The method of claim 13, wherein at least one of the initial volume of fluid and the additional volume of fluid comprises an agent to modulate a permeability of the target vessel.

21. The method of claim 13, further comprising:
evacuating back, through the expandable sheath, a portion of the delivered volume of fluid in order to collapse the expandable sheath; and
removing the apparatus from the target vessel after evacuating the portion of the delivered volume of fluid.

22. The method of claim 13, wherein:
the at least one fluid source includes a first fluid source and a second fluid source;
the initial volume of fluid is delivered from the first fluid source; and
the additional volume of fluid is delivered from the second fluid source.

* * * * *

UNITED STATES PATENT AND TRADEMARK OFFICE
CERTIFICATE OF CORRECTION

PATENT NO. : 7,575,569 B2  Page 1 of 1
APPLICATION NO. : 11/465109
DATED : August 18, 2009
INVENTOR(S) : Christian S. Eversull et al.

It is certified that error appears in the above-identified patent and that said Letters Patent is hereby corrected as shown below:

Column 16
Line 37, delete "volume of fluid and the" and insert -- volume and the -- therefor.

Signed and Sealed this

Thirty-first Day of August, 2010

David J. Kappos
*Director of the United States Patent and Trademark Office*

UNITED STATES PATENT AND TRADEMARK OFFICE
CERTIFICATE OF CORRECTION

PATENT NO.        : 7,575,569 B2
APPLICATION NO.   : 11/465109
DATED             : August 18, 2009
INVENTOR(S)       : Eversull et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 238 days.

Signed and Sealed this

Seventh Day of September, 2010

David J. Kappos
*Director of the United States Patent and Trademark Office*